United States Patent
Mathews et al.

(10) Patent No.: US 6,206,826 B1
(45) Date of Patent: Mar. 27, 2001

(54) DEVICES AND METHODS FOR PERCUTANEOUS SURGERY

(75) Inventors: Hallett Mathews, Richmond, VA (US); Bradley T. Estes, Memphis; Eddie Ray, III, Cordova, both of TN (US); Mingyan Liu, Bourg-la-Reine (FR)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/336,191

(22) Filed: Jun. 18, 1999

Related U.S. Application Data

(63) Continuation of application No. 08/993,186, filed on Dec. 18, 1997, now abandoned.

(51) Int. Cl.$^7$ .................................................. A61B 17/02
(52) U.S. Cl. .......................................... 600/210; 600/221
(58) Field of Search .................................. 600/187, 190, 600/205, 208, 210, 241, 245, 247, 249, 232, 221

(56) References Cited

U.S. PATENT DOCUMENTS

| 465,161 | 12/1891 | Chase | 600/205 |
|---|---|---|---|
| 1,633,443 | 6/1927 | Frangedakis | 600/138 |
| 2,255,657 | 5/1941 | Freedman | 600/249 |
| 2,482,116 | 9/1949 | Lanahan | 600/187 |

(List continued on next page.)

FOREIGN PATENT DOCUMENTS 0 077 159   4/1983  (EP) .

OTHER PUBLICATIONS

Mayer, H. Michael, M.D., "A New Microsurgical Technique for Minimally Invasive Anterior Lumbar Interbody Fusion," SPINE, vol. 22, No. 6, pp. 691–700.

AESCULAP® miaspas mini ALIF Microsurgical Anterior Lumbar Interbody Fusion System, Surgical Technique Brochure, pp. 1–25.

*Primary Examiner*—Paul J. Hirsch
(74) *Attorney, Agent, or Firm*—Woodard, Emhardt, Naughton, Moriarty & McNett

(57) ABSTRACT

A percutaneous surgical system includes a plurality of tissue retractors configured to maintain a working space within soft tissue. The tissue retractors include a prong on their inner surfaces for engaging a ring member. The ring member maintains the position of the tissue retractors while also defining a number of channels inside the ring member. In one embodiment, the ring member includes concentric inner and outer walls connected by support walls. The inner wall defines an inner bore for supporting a working channel sleeve for the introduction of working instruments. A plurality of outer channels are defined between the inner, outer and support walls for the introduction of ancillary instruments to the surgical site. A manipulation tool is also provided that engages each tissue retractor for positioning the retractor within the patient.

15 Claims, 7 Drawing Sheets

U.S. PATENT DOCUMENTS

| | | | |
|---|---|---|---|
| 2,575,253 | 11/1951 | Bicek | 600/210 |
| 2,666,428 | 1/1954 | Glenner | 600/210 |
| 2,756,742 | 7/1956 | Barton | 600/205 |
| 2,829,649 | 4/1958 | Glenner | 600/210 |
| 2,854,004 | 9/1958 | Durrant | 600/205 |
| 3,070,088 * | 12/1962 | Brahos . | |
| 3,570,498 | 3/1971 | Weighton | 600/205 |
| 3,626,471 | 12/1971 | Florin | 600/205 |
| 3,651,800 | 3/1972 | Wilbanks | 600/210 |
| 3,774,596 | 11/1973 | Cook . | |
| 4,049,000 | 9/1977 | Williams | 600/210 |
| 4,232,660 | 11/1980 | Coles | 600/210 |
| 4,344,419 | 8/1982 | Burgin | 600/241 |
| 4,350,151 | 9/1982 | Scott | 600/205 |
| 4,562,832 | 1/1986 | Wilder et al. | 600/205 |
| 4,817,587 | 4/1989 | Janese . | |
| 4,947,896 | 8/1990 | Bartlett | 600/187 |
| 5,027,793 * | 7/1991 | Engelhardt et al. . | |
| 5,035,232 | 7/1991 | Lutze et al. . | |
| 5,125,396 | 6/1992 | Ray . | |
| 5,195,541 | 3/1993 | Obenchain | 128/898 |
| 5,293,863 | 3/1994 | Zhu et al. . | |
| 5,377,667 | 1/1995 | Patton et al. . | |
| 5,381,788 | 1/1995 | Matula et al. . | |
| 5,439,464 | 8/1995 | Shapiro | 606/83 |
| 5,443,058 | 8/1995 | Ough | 600/245 |
| 5,509,893 | 4/1996 | Pracas | 600/224 |
| 5,603,688 | 2/1997 | Upsher | 600/190 |
| 5,846,191 * | 12/1998 | Wells et al. . | |
| 5,846,192 | 12/1998 | Teixido | 600/210 |

* cited by examiner

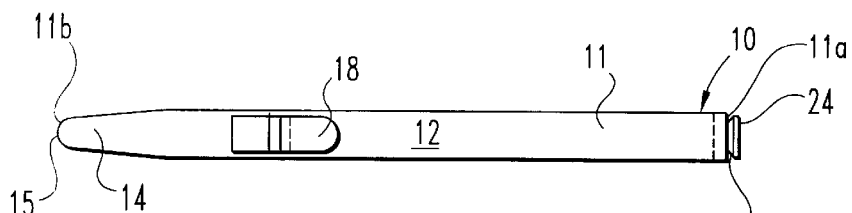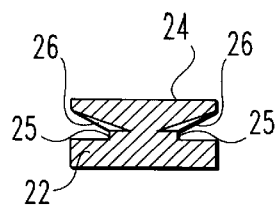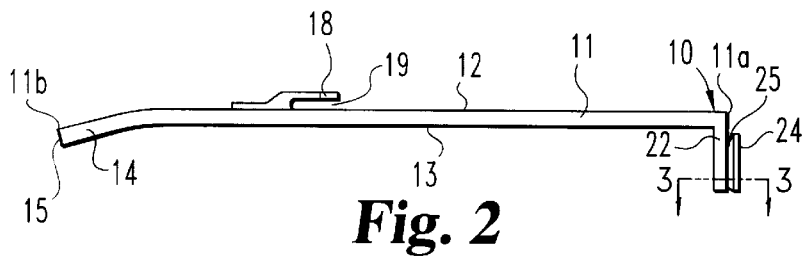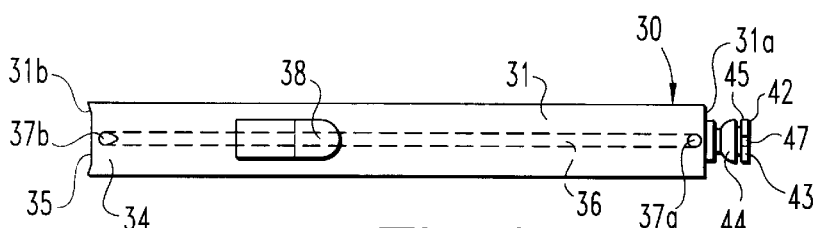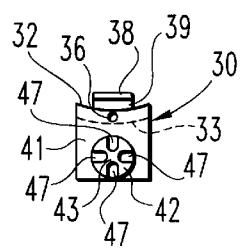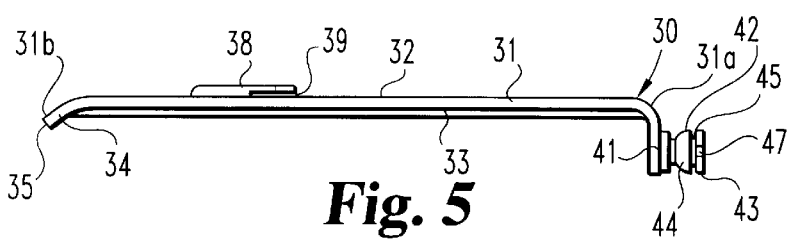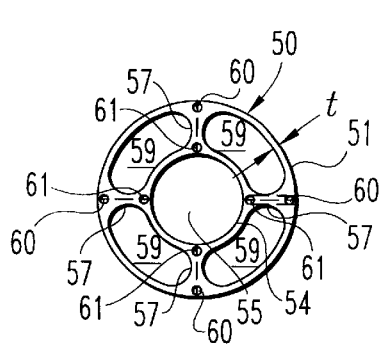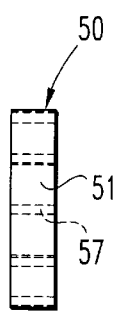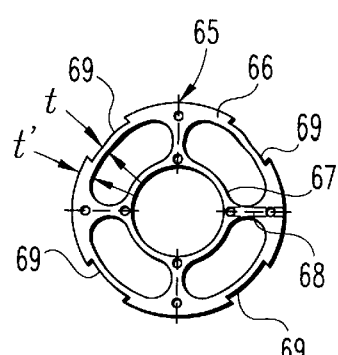

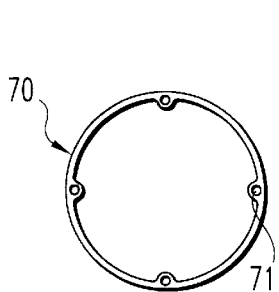
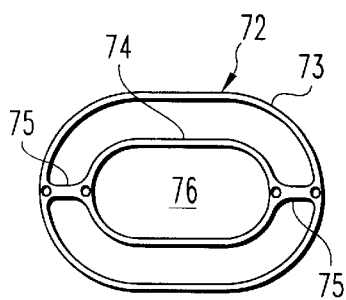
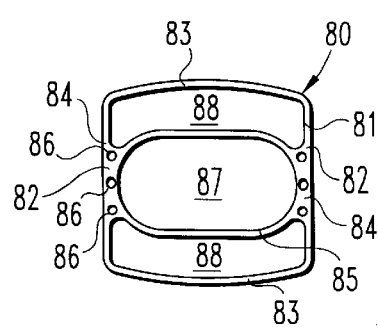
Fig. 10    Fig. 11    Fig. 12
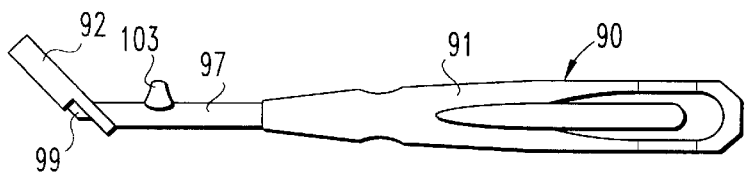
Fig. 13
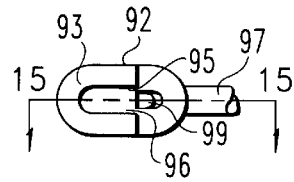
Fig. 14
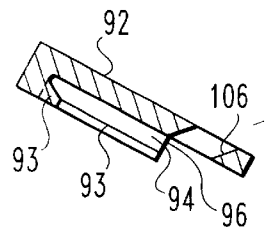
Fig. 15
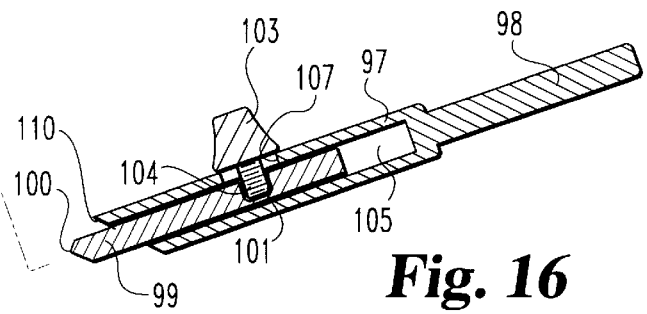
Fig. 16
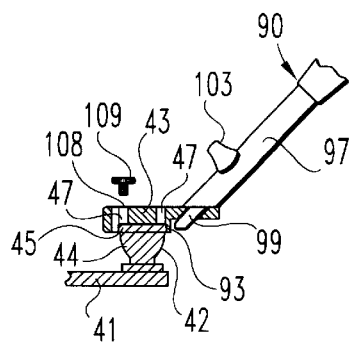
Fig. 17

DEVICES AND METHODS FOR PERCUTANEOUS SURGERY

This application is a continuation of U.S. patent application Ser. No. 08/993,186 filed on Dec. 18, 1997, now abandoned.

FIELD OF THE INVENTION

The present invention relates to devices, instruments and method for performing percutaneous surgeries, particularly at locations deep within the body. One specific application of the invention concerns devices, instruments and techniques for percutaneous, minimally invasive spinal surgery. In another aspect of the invention, the percutaneous surgery is performed under direct vision at any location in the body.

BACKGROUND OF THE INVENTION

Traditional surgical procedures for pathologies located deep within the body can cause significant trauma to the intervening tissues. These open procedures often require a long incision, extensive muscle stripping, prolonged retraction of tissues, denervation and devascularization of tissue. Most of these surgeries require a recovery room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

In a typical open procedure, tissue retractors are used to maintain the working space and provide clearance for various instruments, tools and implants. Typically, several tissue retractors are used to retract skin and muscle layers, as well as vascular and neural structures that may otherwise infringe on the working space. In spinal surgery, exposure of the affected vertebral level, such as for a discectomy and implantation of a fusion cage, can be very involved and can require a complicated array of tissue retractors to maintain the working space.

A common open procedure for disc herniation, laminectomy followed by discectomy, requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of two weeks. In addition to the long recovery time, the destruction of tissue is a major disadvantage of open spinal procedures. This aspect of open procedures is even more invasive when the discectomy is accompanies by fusion of the adjacent vertebrae. Many patients are reluctant to seek surgery as a solution to pain caused by herniated discs and other spinal conditions because of the severe pain sometimes associated with the muscle dissection.

Minimally invasive alternatives, such as arthroscopic or endoscopic techniques, can reduce pain, post-operative recovery time and the destruction of healthy tissue. Orthopedic surgical patients have particularly benefitted from minimally invasive surgical techniques. The site of a pathology is accessed through portals rather than through a significant incision thus preserving the integrity of the intervening tissues. These minimally invasive techniques also often require only local anesthesia. The avoidance of general anesthesia reduces post-operative recovery time and the risk of complications. Minimally invasive surgical techniques are particularly desirable for spinal and neurosurgical applications because of the need for access to locations deep within the body and the range of damage to vital intervening tissues.

In order to further reduce the post-operative recovery time and pain associated with spinal and other procedures, micro-surgical techniques have been developed. For example, in micro-surgical discectomies, the disc is accessed by cutting a channel from the surface of the patient's back to the disc through a small incision. An operating microscope or loupes is used to visualize the surgical field. Small diameter micro-surgical instruments are passed through the small incision and between two laminae and into the disc. The intervening tissues are disrupted less because the incision is smaller. Although these micro-surgical procedures are less invasive, they still involve some of the same complications associated with open procedures, such as injury to the nerve root and dural sac, perineural scar formation, reherniation at the surgical site and instability due to excess bone removal.

The development of systems for performing percutaneous spinal procedures has yielded a major improvement in reducing recovery time and post-operative pain because they require minimal, if any, muscle dissection, and they can be performed under local anesthesia. One such newly developed system is the MED™ Micro Endoscopic Discectomy System manufactured and sold by Sofamor Danek Co., Inc. of Memphis, Tenn. The MED™ System includes a large working channel cannula that is disposed percutaneously so that its distal end is at the surgical site. The large working channel permits the introduction of multiple surgical instruments, including an endoscope to permit direct visualization of the surgical site. As with most percutaneous or endoscopic systems, the MED™ System relies upon indirect visualization techniques, such as lateral fluoroscopy, to orient the large working channel cannula. In addition, like other percutaneous techniques, the MED™ System is inserted into the patient through a small incision.

In recent years, laparoscopic surgery has been employed to treat various anterior pathologies. However, these particular procedures are very difficult to learn and often require the assistance of a general surgeon. In addition, they often result in an increase of operative time because of the difficulty of these techniques.

Although the MED™ System has taken a great step toward advancing the field of percutaneous or endoscopic systems and techniques, it is not the answer for all surgical procedures or for all surgeons. For example, many surgeons have difficulty mastering the techniques associated with percutaneous surgical instruments. In addition, certain surgical procedures require a larger working space than many percutaneous systems can accommodate.

Consequently, there is a need for a system and associated techniques that combine the beneficial aspects of both open surgical techniques and percutaneous surgical techniques. There is a further need for a surgical system that can be readily and easily mastered by all surgeons of various skill levels.

SUMMARY OF THE INVENTION

With the present invention, a system has been developed that gives a surgeon the aforementioned advantages of endoscopic surgery via a retractor system which uses blades similar to that of an open procedure. This system significantly reduces the amount of time needed to learn the procedure and decreases the time of the procedure in the operating room.

In a system according to the present invention, a plurality of tissue retractors are provided for holding and supporting soft tissue for access to a surgical site. A ring member is engaged to and supported by the tissue retractors. The ring member helps maintain a specific positional relationship of the tissue retractors at the surgical site. Moreover, the ring member defines the general confines of a working channel for insertion of various percutaneous instrumentation.

In a further aspect of the invention, a manipulation tool is provided for manipulating the tissue retractors. The manipulation tool can be utilized immediately upon insertion of the tissue retractors into the surgical site to help expand the working channel. Alternatively, the manipulation tool can be used to move the tissue retractors when they are engaged to the ring member.

An important component of the system according to the present invention is the ring member. The ring member not only supports and aligns the tissue retractors, it also provides means for creating not only a working channel, but also a working space for the insertion and manipulation of various surgical tools. For instance, the ring member can support a central sleeve that can constitute a component of a percutaneous surgical system. In addition, the ring member can delineate additional channels outside a central working channel through which ancillary instruments can be inserted and guided to the surgical site.

One object of the invention is to provide devices and methods for percutaneous minimally invasive surgery useful for all applications and approaches. A further object is realized in techniques and instruments that permit surgical procedures in the working space under direct vision.

Yet another object is to reduce the number of entries into the patient for a particular surgical procedure. The fields of spinal and neuro surgery are particularly benefitted by devices and techniques according to the present invention that minimize the invasion into the patient, that are streamlined and concise in their application, and that can be easily mastered by the surgeon. Other objects and benefits of this invention can be discerned from the following written description and accompanying figures.

DESCRIPTION OF THE FIGURES

FIG. 1 is a top elevational view of a tissue retractor in accordance with one embodiment of the present invention.

FIG. 2 is a side elevational view of the tissue retractor shown in FIG. 1.

FIG. 3 is a side cross-sectional view of a portion of the tissue retractor shown in FIG. 2 taken along line 3—3 as viewed in the direction of the arrows.

FIG. 4 is a top elevational view of a tissue retractor according to a further embodiment of the invention.

FIG. 5 is a side elevational view of the tissue retractor shown in FIG. 4.

FIG. 6 is a top view of the tissue retractor shown in FIGS. 4 and 5.

FIG. 7 is a top elevational view of a ring member used with tissue retractors constructed according to the principles of FIGS. 1–6.

FIG. 8 is a side elevational view of the tissue retractor shown in FIG. 7.

FIG. 9 is a top elevational view of a ring member according to an alternative embodiment of the present invention.

FIG. 10 is a top elevational view of a ring member according to a further embodiment of the present invention.

FIG. 11 is a top elevational view of still another embodiment of a ring member according to still another embodiment of the present invention.

FIG. 12 is a top elevational view of a ring member according to an additional embodiment of the present invention.

FIG. 13 is a side elevational view of a manipulation tool according to one embodiment of the present invention for manipulating the tissue retractors constructed according to FIGS. 1–6.

FIG. 14 is an end elevational view of one end of the manipulation tool shown in FIG. 13.

FIG. 15 is a side cross-sectional view of the base of the manipulation tool shown in FIGS. 13 and 14, taken along line 15—15 as viewed in the direction of the arrows.

FIG. 16 is a cross-sectional view of the stem component of the manipulation tool shown in FIG. 13.

FIG. 17 is a side partial cross-sectional view of one embodiment of the manipulation tool shown in FIG. 13 engaged to the embodiment of the tissue retractor shown in FIGS. 4–6.

DESCRIPTION OF THE PREFERRED EMBODIMENTS

Figure 18:
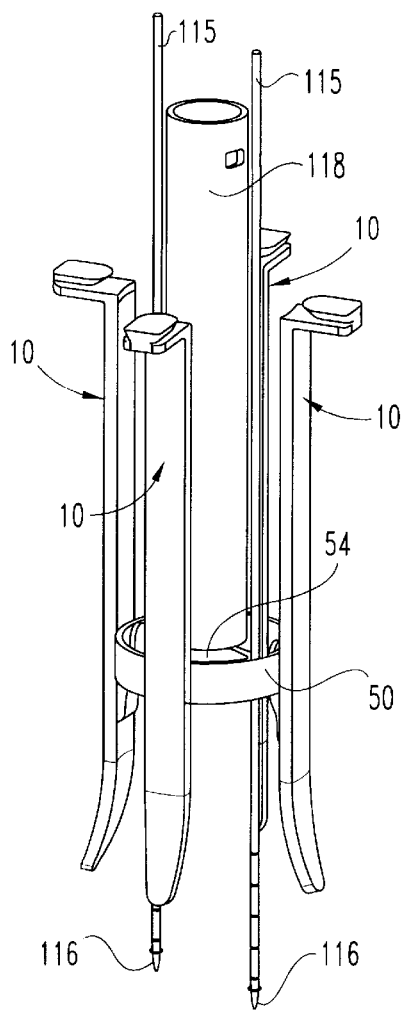
FIG. 18 is a side perspective view of a tissue retraction system according to one embodiment of the invention utilizing tissue retractors constructed according to FIGS. 1–3 and a ring member constructed according to FIGS. 7–8 in combination with a working channel sleeve.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention contemplates devices and methods for percutaneous surgery in a wide variety of surgical arenas. The following description will focus upon apparatus and techniques for performing percutaneous spinal surgery, such as a discectomy and interbody fusion. It is understood that the invention can be applied to a variety of surgical procedures at many locations in the body.

In accordance with one embodiment of the invention, a tissue retractor 10 is provided as depicted in FIGS. 1–3. The tissue retractor 10 includes an elongated blade 11 that is sized for introduction through an incision or opening in a patient's skin in soft tissue. In a specific embodiment, the tissue retractor blade 11 has a length of about 180 mm so that the proximal end 11a of the blade is disposed above the patient's skin while the distal end 11b is disposed immediately adjacent the desired surgical site. It is understood that a variety of lengths of blades 11 can be provided for the tissue retractors 10, depending upon the surgical procedure to be conducted and the surgical approach to be implemented.

The blade 11 of the retractor 10 includes an inner surface 12 and an opposite retraction surface 13. The retraction surface 13 is configured for intimate contact with the soft tissue to be retracted. The blade 11 also includes an end portion 14 at the distal end 11b of the blade which is preferably configured for atraumatic introduction to a surgical site. In one specific embodiment, the end portion 14 has a rounded or blunt tip 15. In addition, in the embodiment illustrated in FIG. 2, the end portion 14 is angled slightly away from the inner surface 12. This angular orientation of the end portion 14 facilitates manipulation of the soft tissue as the tissue retractor 10 is inserted into the patient. Moreover, the angled end portion 14 helps maintain the surgical site free from incursion of the adjacent soft tissues.

In one important feature of the present invention, the tissue retractor 10 includes a prong 18 attached to and projecting from the inner surface 12. The prong is configured to define a slot 19 between the prong and the inner surface 12. As explained in more detail herein, the prong is configured to support a ring member, and is consequently sized accordingly. In one specific embodiment, the slot 19 defined by the prong 18 has a length of about 14 mm and a height dimension (separation from the inner surface 12) of about 3 mm.

In certain embodiments of the invention, the tissue retractor 10 includes means for engagement to a manipulation tool. For example, as depicted in FIGS. 1–3, the tissue retractor 10 includes a plate portion 22 that projects generally perpendicularly from the proximal end 11a of the blade 11. In the illustrated embodiment, the plate projects outward away from the inner surface 12 of the blade. In this manner, the plate portion will not interfere with the working space defined between the several tissue retractors 10 disposed within a patient. A boss 24 projects from the plate portion 22 away from the proximal end 11a of the blade 11. In the preferred embodiment, and as shown in greater detail in FIG. 3, the boss defines a groove 25 between the boss and the plate portion 22. In the specific embodiment, the boss further defines dovetail surfaces 26 that taper toward the plate portion 22. The dovetail surfaces 26 operate as wedging surfaces for engagement by a manipulation tool as described further herein.

An alternative embodiment of a tissue retractor 30 is shown in FIGS. 4–6. The tissue retractor 30 includes an elongated blade 31 that defines an inner surface 32 and an outer surface 33. The inner surface 32 can be arcuate, and specifically concave to accommodate the ring member described herein. Like the tissue retractor 10, this alternative retractor 30 also includes a prong 38 projecting from the inner surface 32 which defines a slot 39 therebetween. The blade 31 can be sized in a similar fashion to the blade 11 of the tissue retractor 10 as described above.

The tissue retractor 30 includes a distal end portion 34 of the blade 31 that is configured differently from the distal end portion 14 of the previous embodiment. In this version, the tip 35 of the end portion 34 is not rounded, but is instead generally linear. While the tissue retractor 10 is well suited for retraction of vessels and nerves, the tissue retractor 30 is best suited for the complete retraction of soft tissue surrounding the surgical site. As a further modification, the end portion 34 is formed or curved to a radius, rather than bent at an angle as in the tissue retractor 10.

In a further modification from the prior embodiment, the tissue retractor 30 includes a bore 36 extending along substantially the entire length of the blade 31, in other words from the proximal end 31a to the distal end 31b. The bore 36 is open at both ends. In particular, the bore defines a bore opening 37a at the proximal end and 37b at the distal end. At the distal end, the bore 36 intersects the end portion 34 to define the bore opening 37b. The bore 36 is particularly sized to receive an elongated pin, such as a Steinmann pin. In this manner, the tissue retractor 30 can be anchored to a particular position by way of the Steinmann pin. Specifically, the tissue retractor 30 can be introduced through a skin incision and directed to the surgical site. When the tissue retractor 30 is manipulated to its operative position, the fixation pin can be extended through the bore 36 with the tip of the pin penetrating an adjacent bony structure to anchor the tissue retractor 30 in place. Alternatively, the bore 36 can be provided with internal threads to mate with external threads on an intermediate portion of the elongated pin. With this modification, the pin is advanced by screwing into the bore 36. Preferably, the tip of the pin also includes self-tapping threads to drive into the bone. In this manner, the retractor assembly will be fully anchored at the surgical site.

Like the tissue retractor 10, the alternative embodiment retractor 30 also includes means for engagement by a manipulation tool. The tissue retractor 30 includes a plate portion 41 that projects perpendicularly from the blade 31. A boss 42 is attached to the plate portion 41 and projects away from the proximal end 31a of the blade. The boss 42 is formed by a disc 43 attached to a base 44, separated by a groove 45. Preferably, the groove 45 is generally coincident with the perimeter of the disc 43. The groove 45 formed between the disc 43 and base 44 is configured to receive a portion of a manipulation tool, as discussed more fully herein. The disc 43 also defines the plurality of notches 47 that pass through the disc toward the base 44, intersecting the groove 45. Again, the notches 47 are configured for engagement by a manipulation tool discussed herein.

A second important component of the system according to the present invention is a ring member, such as the ring member 50 depicted in FIGS. 7 and 8. In accordance with the present embodiment, the ring member includes a generally circular outer wall 51 having a thickness t. The thickness t of the wall is calibrated to fit within one of the slots 19, 39 of the tissue retractor 10, 30. In one specific embodiment, this thickness t is 2.0 mm. This 2.0 mm thickness of the outer wall 51 of the ring member 50 allows a certain degree of play in the slot, such as slot 19 having a width of about 3 mm. Part of this play is necessary because the inner surface 12 of the tissue retractor 10 is generally flat, while the outer wall 51 of the ring member 50 is curved.

The ring member is also defined by an inner wall 54 that is generally circular, in the preferred embodiment, and is concentrically disposed within the outer wall 51. The inner wall 54 defines an inner channel 55 at the interior of the wall. The outer wall 51 and inner wall 54 are joined by a number of support walls 57. In the illustrated embodiment, four such support walls 57 are uniformly distributed at 90 degree intervals to support the inner wall 54 concentrically within the outer wall 51. Of course, it is understood that the arrangement of support walls 57 can be modified to achieve different orientations of the inner wall 54 relative to the outer wall 51. Likewise, the configuration of the support walls 57 can be varied depending upon the configuration of either or both of the inner wall 54 and outer wall 51.

In the embodiment illustrated in FIGS. 7 and 8, the outer wall 51, inner wall 54 and support walls 57 define a number of outer channels 59 that are outside the inner wall 54, but inside the outer wall 51. These outer channels are sized and configured to allow a surgeon to introduce ancillary tools and instrumentation through the channels and to the surgical site being maintained by the tissue retractors 10, 30. In a further aspect of this embodiment of the ring member 50, pin bores 60 are provided at the outer wall 51 and pin bores 61 are defined at the inner wall 54, all being sized to receive a fixation pin, such as the Steinmann pin discussed above. The number of outer bores 60 and inner bores 61 facilitate anchoring the ring member 50 to the surgical site, such as by driving a Steinmann pin into adjacent bone. The array of outer bores and inner bores 61 give the surgeon great flexibility in deciding where to place a fixation pin, depending upon the underlying anatomy. For example, one fixation pin can be extended through an outer bore 60, while another pin can be extended through an inner bore 61 that is diametrically opposite from the other fixation pin. Depending upon the degree of support required, fixation pins can be limited to only a few of the bores 60, 61, or can be engaged in all of the bores.

In the embodiment of the ring member 50, the outer wall 10, 51 can be received within the prongs 18, 38 at any location around the perimeter of the outer wall 51. In an alternative embodiment, a ring member 65 is provided that limits or restricts the location of the tissue retractors 10, 30. Specifically, the ring member 65 includes an outer wall 66 and an inner wall 67 connected by support walls 68, all in a manner similar to the ring member 50. However, in this embodiment, the outer wall 66 defines a number of peripheral notches 69 formed in the outer surface of the outer wall 66. These peripheral notches 69 are sized to receive one of the tissue retractors 10, 30, and particularly the blades 11, 31 of those retractors, therein. The outer wall 66 has a thickness t that is equivalent to the thickness t of the outer wall 51 of the prior ring member 50. In order to define the peripheral notches 69, the outer wall includes sections having a larger thickness t' that is at least thicker than the width of the slots 19, 39 in either of the tissue retractors 10, 30. Thus, while in the embodiment of FIGS. 7 and 8, the ring member 50 permits movement of a tissue retractor around the circumference of the outer wall 51, the ring member 65 restricts the location of the tissue retractors to fixed positions within a corresponding peripheral notch 69.

The present invention contemplates further alternative embodiments of a ring member used with the tissue retractors 10, 30. For example, an open ring member 70 is depicted in FIG. 10. This open ring member 70 does not include an inner wall as with the previous two embodiments. The ring member 70 can include pin bores 71 for receiving fixation pins as described above.

A double-barrel ring member 72 is illustrated in FIG. 11. In this embodiment, the outer wall 73 and inner wall 74 are generally oval in configuration. The two walls are joined by a number of support walls 75. The inner wall 74 defines an inner channel 76 that is oblong and is preferably sized to receive two or more sleeves, cannulae or trocars. The sleeves can be separate parts or integrally formed. This is in contrast to the ring members 50 and 65 in which the respective inner walls 54, 67 are generally configured to receive but a single sleeve or tubular member.

A related ring member 80 is depicted in FIG. 12. In this embodiment, the inner wall 85 defines an oblong inner channel 87 that is configured to receive multiple tubular elements or sleeves therein. In this embodiment, however, the outer wall 81 is configured differently from the outer walls of the previous embodiments. Specifically, the outer wall 81 includes opposite flat sidewalls 82 and intermediate opposite curved side walls 83. In other words, the outer wall 81 has the configuration of a slightly bowed rectangular shape. In this embodiment, the outer wall 81 and inner wall 85 are joined at two support walls 84 that give the appearance of an enlarged region joining the inner and outer walls. In accordance with this embodiment, a number of pin bores 86 can be formed generally within these enlarged regions or support walls 84. In this embodiment, two outer channels 88 are defined between the outer wall 81 and the inner wall 85. As can be seen in FIG. 12, the outer channels are substantially rectangular in configuration.

In order to facilitate usage of the components of the present inventive system, manipulation tools are provided for manipulating the tissue retractors 10, 30. One embodiment of a manipulation tool 90 according to the present invention is shown in FIGS. 13–17. The manipulation tool 90 includes a handle 91 configured to be manually grasped by the surgeon or surgical assistant. A base 92 is attached to the handle 91. The base 92 defines an in-turned flange 93 that defines a recess 94 between the base and the flange and a slot 95 that is open to the recess 94. The recess 94 is also open at one end so that the flange 93 is not continuous about the entire base 92.

The manipulation tool further includes a stem 97 with a handle interface 98, as shown most clearly in FIG. 16. The handle interface 98 can be press-fit into a corresponding bore within the handle 91. A plunger 99 is slidably disposed within a stem bore 105 in the stem 97. The plunger 99 has a tip 100 that can be suitably configured to contact the boss 24, 42 of a tissue retractor 10, 30.

The plunger 99 further includes a threaded bore 101 that is oriented transverse to the longitudinal axis of the plunger. The threaded bore 101 is configured to receive the threaded stem 104 of a release pin 103, again as shown in FIG. 16. The threaded stem 104 projects through a locking bore 107 in the stem 97 so that the threaded stem 104 can be engaged within the threaded bore 101.

As shown in FIGS. 15, 16, the end 110 of the stem 97 is angled to mate with the base 92. In accordance with the present invention, the stem 97 is oriented so that the stem bore 105 is concentric with a plate bore 106 in the base 92. In this configuration, then, the plunger 99 can be projected from the stem bore 105 through the plate bore 106 so that the tip 100 of the plunger 99 is disposed at the open end of the recess 94. In this manner, the manipulation tool 90 can be used to engage the boss 24, 42 of a tissue retractor 10, 30. For example, as shown in FIG. 17, the manipulation tool 90 is shown engaged to the boss 42 of a tissue retractor such as the tissue retractor 30. In this embodiment, the disc 43 of the boss 42 is disposed within the recess 94 defined by the flange 93. The disc 43 is sized so that it cannot be withdrawn through the slot 95, but must instead enter the recess 94 through the end opening 96. It is understood that the flange 93 of the manipulation tool 90 engages the groove 45 of the boss 42 of the tissue retractor 30.

Once the boss 42 is fully seated within the recess 94 of the manipulation tool 90, the plunger can be extended through the plate bore 106 until the tip 100 of the plunger is essentially blocking the end opening 96 of the recess 94. Thus, the boss 42 cannot be removed from the recess 94 of the manipulation tool 90 unless and until the plunger 99 is retracted.

In a further feature, the base 92 of the manipulation tool 90 can be provided with a bore 108 at the closed end of the recess 94. The bore 108 is sized to receive a locking pin 109. The bore 108 is oriented to align with one of the notches 47 defined in the disc 43 of the boss 42. Insertion of the locking pin 109 prevents rotation of the boss 42, and consequently of the manipulation tool 90 relative to the tissue retractor 30.

With these details of the components of the present inventive system, the use of these components can now be described. First, with reference to FIGS. 18, 19, it can be seen that four tissue retractors 10 are engaged to a ring member 50. Specifically, as can be seen in the top view of FIG. 19, the outer wall 51 of ring member 50 is situated within the slots 19 formed by the prongs 18. As can be seen in this Figure, the tissue retractors 10 can be moved about the outer wall 51 in the direction of the arrows A. In the illustrated configuration, a pair of guide pins 115 are extended through one of the pin bores 60, 61. The guide pins 115 each include a sharp or tapered tip 116 that is preferably configured to penetrate bone. Alternatively, the tip 116 can include self-tapping threads for screwing the pins into the bone.

Figure 19:
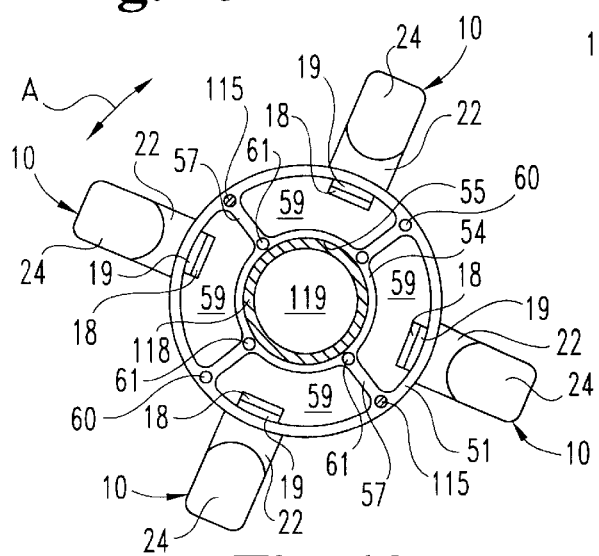
FIG. 19 is a top elevational view of the tissue retraction system shown in FIG. 18.
Figure 20:
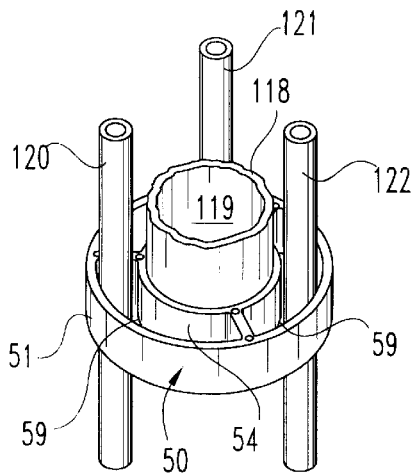
FIG. 20 is a side perspective partial cut away view of a ring member in accordance with FIGS. 7–8 with additional components disposed within the ring member.

The assembly depicted in FIGS. 18 and 19 also includes a sleeve 118 that is guided and/or supported by the inner wall 54 of the ring member 50. Specifically, the sleeve 118 is a tubular member that can be slidably disposed within the inner channel 55 of the ring member 50. The sleeve 118 itself defines a working channel 119 along its length. In one specific embodiment, the sleeve 118 has an outer diameter that is sized for a pressfit engagement with the inner wall 54 within the inner channel 55. Alternatively, the sleeve 118 can be sized to slide freely through the inner channel 55. In this instance, the sleeve 118 can be provided with some form of stop on the outer surface of the sleeve to restrict the depth of insertion of the sleeve into the working site. It is understood that one aspect of the invention is that the outer channels 59 of the ring member 50 provide access for ancillary instrumentation to the surgical site. At the same time, the sleeve 118 defines a working channel 119 for various percutaneous instrumentation. It is therefore advantageous that the sleeve 118 be supported far enough away from the primary working site to permit access to that site by way of the outer channels 59. This concept is illustrated in FIG. 20. This figure is focused upon the ring member 50 and is illustrated without the tissue retractors 10 in their operative position. As shown in FIG. 20, the sleeve 118 is supported by the inner wall 54. At the same time, a suction tube 120 is situated within one outer channel 59, and irrigation tube 121 is situated in another outer channel, and a visualization instrument 122 is extended through still another outer channel 59. With this arrangement, working tools can be extended into the working channel 119 through the sleeve 118 while the ancillary instrumentation for providing irrigation and suction as well as the visualization, are supported for direct access to the site. This particular feature of the present invention provides a substantial benefit over both prior open surgical procedures and prior percutaneous surgical procedures. First, the present invention provides for a minimal intrusion into the patient. The use of the tissue retractors 10, 30 and the ring member 50 minimizes the surgical incision necessary to access the ultimate surgical site. Providing a sleeve with a working channel emulates the typical percutaneous surgical approaches of prior techniques.

At the same time, the ring member acts as a guide not only for the tissue retractors, but also for ancillary instrumentation that are not in themselves directly involved in the surgical process. The irrigation and aspiration that would normally occupy a certain amount of space within the working channel 119 of the sleeve 118 in a typical percutaneous procedure, are now moved outboard of the working channel but are still intimately associated with the working channel and the operative instruments and tools. Likewise, the visualization instrument 122 is moved outside of the working channel to make room for the operative tools, but is still supported to provide for direct viewing of the surgical site. In some applications, moving the visualization instrument 122 outboard of the working channel can provide a better, almost panoramic, view of the surgical site.

Moreover, the provision of multiple outer channels 59 allows the surgeon to remove the visualization instrument 122 from one channel and move it to another channel for a different or better view of the surgical procedure being undertaken. Most prior percutaneous or endoscopic surgical instruments require manipulation of the endoscope or working channel itself in order to alter the viewing angle and viewing area. In this respect, the present invention emulates an open surgical procedure in which the surgeon has a wider more accessible surgical site within which to manipulate the various ancillary instruments necessary for any surgical procedure. Although the focus of the present preferred embodiment is on extending ancillary instrumentation through the outer channel 59, it is of course contemplated that working tools themselves could also be passed through an outer channel 59 to the surgical site. This flexibility is again one of the features of the present invention that emulates the typical open surgical procedure.

Figure 21:
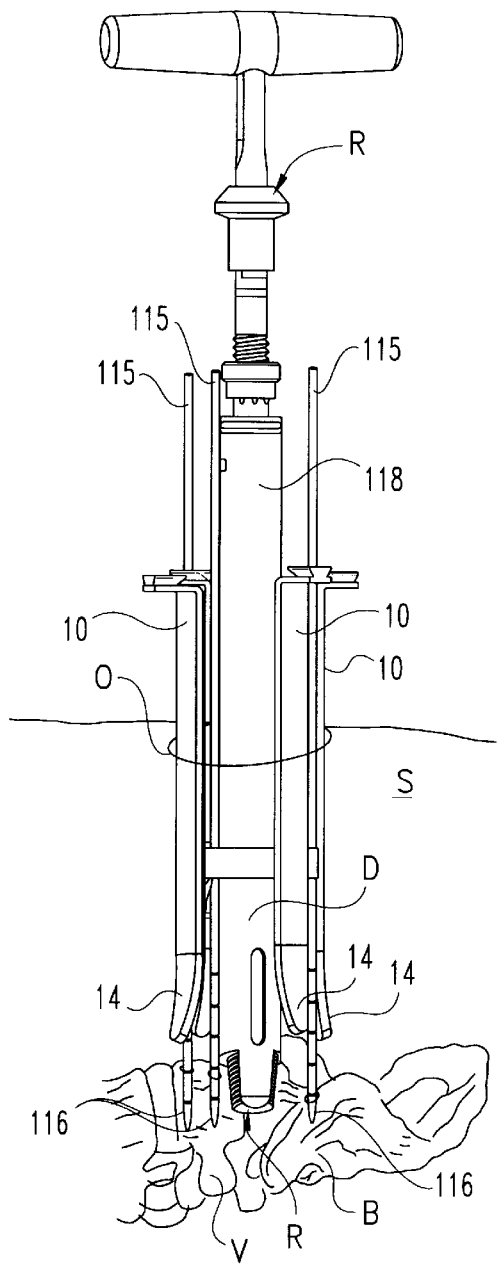
FIG. 21 is a side elevational view of the tissue retraction system shown in FIGS. 18–19 situated within a patient for performing a surgical procedure in the disc space between the L5 lumbar vertebra and the sacrum.

One specific application of the apparatus of the present invention is shown in FIG. 21. In this procedure, a bore is created in the L5-S1 disc space for eventual implantation of a fusion cage, for example. In this procedure, a guide needle can first be inserted into the patient directly into the L5-S1 disc space. An incision can be made at the site of insertion of the needle for receipt of a dilator. The dilator is introduced over the needle and through the skin incision until the tip of the dilator rests upon the disc annulus. In one specific embodiment, the dilator can have an outer diameter of 10–12 mm. In the next step, the large dilator is removed and a smaller dilator introduced over the guide needle. In this specific embodiment, the smaller dilator has an outer diameter of 4 mm.

With the small dilator in place, the guide needle can be removed or retained in position as desired by the surgeon. At this time then, the tissue retractors 10 can be introduced through the incision or opening O in the skin S. In a preferred embodiment, four separate blades are inserted into the skin opening. Using a manipulation tool, such as tool 90, or another distraction apparatus, the tissue retractors 10 are moved outward, or dilated, so that the opening O in the skin is enlarged to a desired dimension. With the tissue dilators 10 in position, the ring member 50 can be introduced through the opening O and between each of the dilators. The ring member 50 is slid within the space defined by the tissue retractors until it comes to rest within the slot 19 defined by each of the prongs 18 of the tissue retractors 10. At this point, the ring member is properly seated and the tissue retractors 10 are now effectively supported in their final position to maintain a clear working space through the skin S and to the working site.

At this point, the ring member 50 can be anchored into position by extending guide pins 115 through appropriate pin bores 60 or 61 in the ring member. The tips 116 of corresponding guide pins can penetrate the L5 vertebra V and/or the sacrum B as desired to firmly fix the surgical construct in position. It is understood that alternatively, tissue retractors such as retractors 30 shown in FIGS. 4–6 could be used. These tissue retractors include a bore 36 through which the guide pins 115 could be extended for anchoring in the underlying bone.

With the ring member 50 properly anchored, the working tools and instrumentation can now be percutaneously introduced to the surgical site. For instance, a distraction tool D can be extended through the working channel 119 defined by the sleeve 118 supported by the ring member 50. The distraction tool D can be used to distract the affected disc space. Prior to use of the distraction tool, other tools and instruments can be inserted through the working channel for performing an annulotomy and discectomy at the surgical site. Once the distraction tool is in place, a reaming tool R can be extended through both the distraction tool D and the working channel sleeve 118, all again supported by the ring member 50 and the tissue dilators 10. Once the adjacent bone V and B have been reamed, the reaming tool R can be removed and another tool used to insert a fusion cage into the surgical site.

In some procedures, fusion devices can be placed bilaterally within a disc space. In this instance, the double barrel ring member, such as member 72 shown in FIG. 11, can be used. In this case, two sleeves 118 can be supported within the inner wall 74. The two sleeves can also be provided integrally formed as a single double barrel unit. The distraction tool D and reaming tool R can be sequentially extended through each of the two working channel sleeves 118 to prepare the bilateral cage placement sites.

Figure 23:
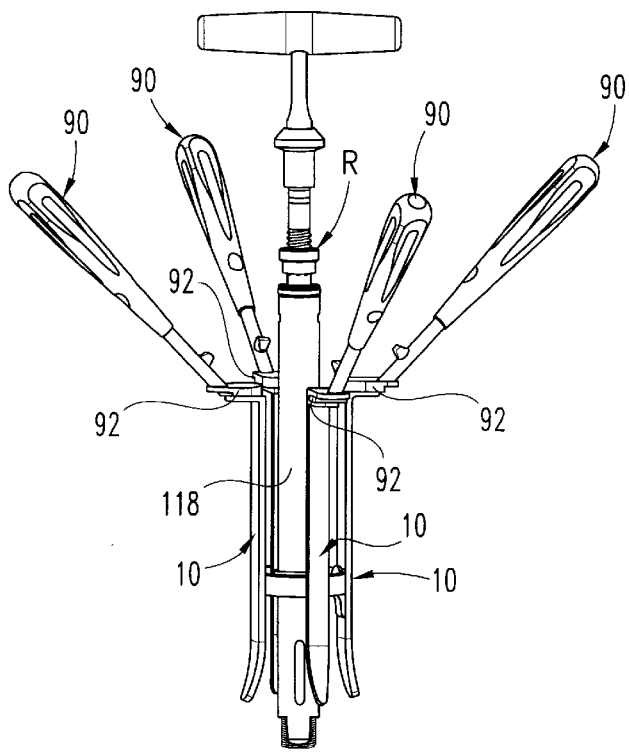
FIG. 23 is a side perspective view of a tissue retraction system in accordance with FIGS. 18–20 shown with manipulation tools according to FIGS. 13–16 engaged to the ends of the tissue retractors.
Figure 22:
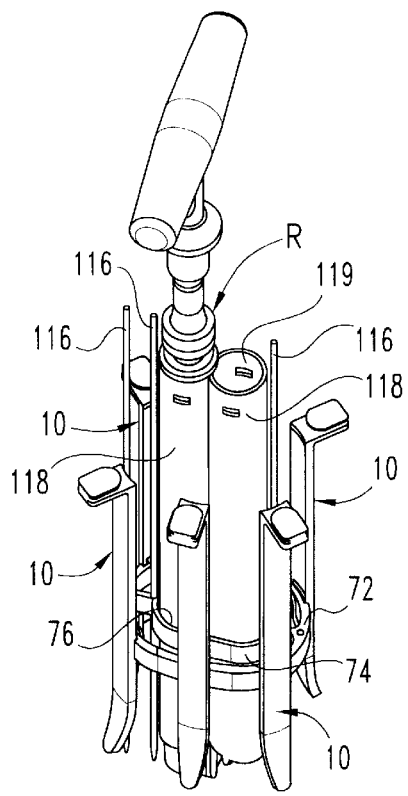
FIG. 22 is a top perspective view of a tissue retraction system according to a further embodiment particularly utilizing a ring member constructed in accordance with FIG. 11.

The implementation of the manipulation tool 90 with respect to the tissue retractors 10 is shown in FIG. 23. In this arrangement, the manipulation tools 90 are engaged to the tissue retractors 10 while the surgical instruments, such as the reamer R, are supported by the assembly. In this manner, the tissue retractors 10 can be manipulated during the surgical procedure as may be necessary to modify the working area and surgical site. For example, in some instances when a visualization instrument is extended through the outer channels 59 of the ring member 50, the view of the instrument may be blocked by adjacent soft tissue. One or more of the tissue retractors 10 can be moved using the manipulation tool 90 to push aside the infringing soft tissue. The manipulation tools can be used to orient the tissue retractors 10 prior to addition of the ring member 50. In addition, the ring member 50 can be used as a fulcrum in situ to pivot the tissue retractors 10.

Figure 24:
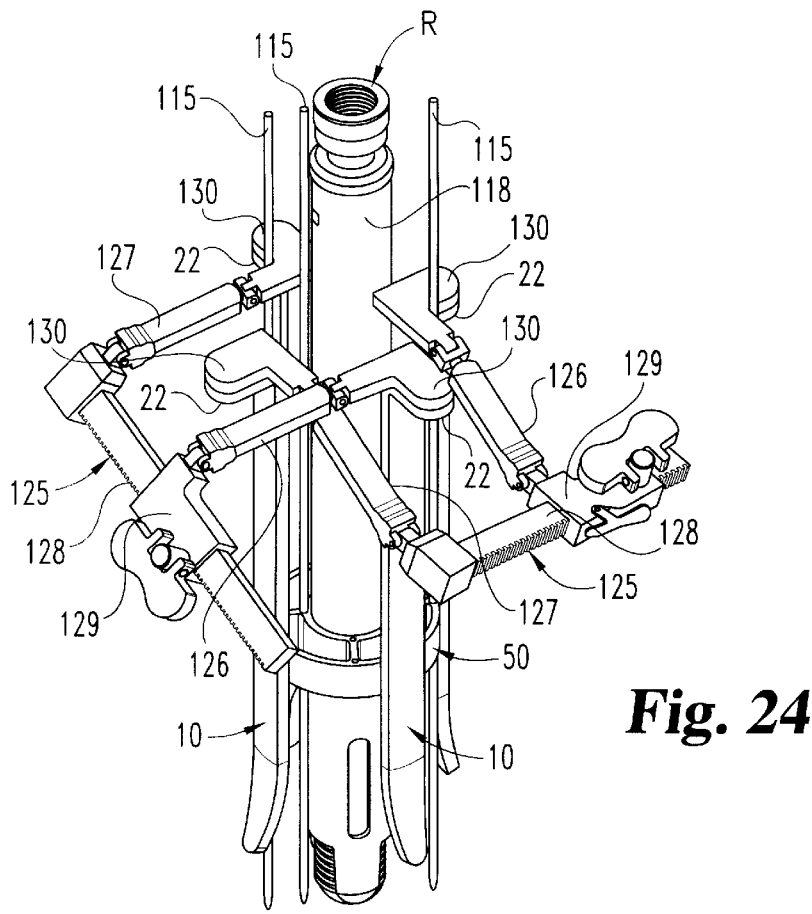
FIG. 24 is a top perspective view of a tissue retraction system according to an additional embodiment of the invention with self-retaining retractors engaged to the tissue retractors.

In an additional embodiment, the manipulation tools 90 are replaced by self-retaining retractor assemblies 125. As depicted in FIG. 24, two such retractor assemblies 125 can be engaged to the bosses 24 of tissue retractors 10 on opposite sides of the ring member 50. The retractor assembly includes a movable arm 126 and a fixed arm 127. A ratchet bar 128 extends from the fixed arm 127. The movable arm includes a ratchet lock mechanism 129 that allows the movable arm 126 to be moved incrementally along the ratchet bar 128 and fixed in a specific position. Each of the arms 126, 127 of both retractor assemblies 125 includes a mating adapter 130 that is configured to fit over the boss 24 of the tissue retractor 10. The mating adapter 130 can have the same cross-sectional appearance as the base 92 of the manipulation tool 90, depicted in FIG. 15.

The self-retaining retractor assemblies 125 provide a further method for manipulating the tissue retractors at the surgical site. Specifically, the movable arms 126 can be moved away from the fixed arms 127 to distract the opposite tissue retractors 10. An array of tissue retractor assemblies 125 can be provided depending upon the number of tissue retractors 10 to be distracted. Preferably, the self-retaining retractor assemblies 125 remain connected to the tissue retractors 10 throughout the surgical procedure in order to maintain the distraction of the retractor blades and to ultimately maintain the working space.

Figure 25:
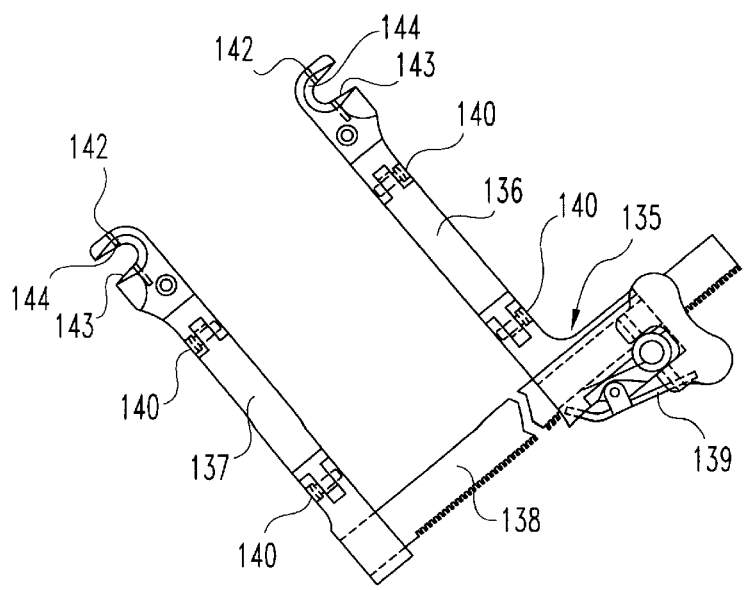
FIG. 25 is a top elevational view of a self-retaining retractor configured for use with the tissue retraction system shown in FIG. 18, for example.

An alternative embodiment of a self-retaining retractor assembly is shown in FIG. 25. This retractor assembly 135 includes a movable arm 136, a fixed arm 137 and a ratchet bar 138 extending from the fixed arm upon which the movable arm slides. A ratchet lock mechanism 139 locks the movable arm 136 to the ratchet bar 138. The arms also include a number of pivots 140 to permit changing the orientation of the self-retaining retractor assembly 135 as required for engagement to tissue retractors. The retractor assembly 135 includes mating adapters 142 at the end of each of the movable and fixed arms 136, 137. In the preferred embodiment, the mating adapters 142 include an engagement slot 143. The adapters also define a beveled wedging surface 144 surrounding the engagement slot 143. This particular embodiment is configured to engage the boss 42 of the tissue retractor 30 depicted in FIGS. 4–6. The self-retaining retractor assembly 135 can be operated in the same manner as the retractor assembly 125 discussed above.

The invention further contemplates the use of an external device to support a retractor assembly at a surgical site. For example, various rigid or flexible arms have been provided that are grounded to an external frame or to the surgical table. The free end of the support arm can be modified to include a mating adaptor end similar to the adaptors 130, 142 shown in FIGS. 24, 25, respectively. The support arm can then be engaged to an individual retractor blade to support the blade at the surgical site. This external support can be maintained throughout the surgery or can be removed once the tissue retractor assembly has been anchored to the patient's bone.

Figure 26:
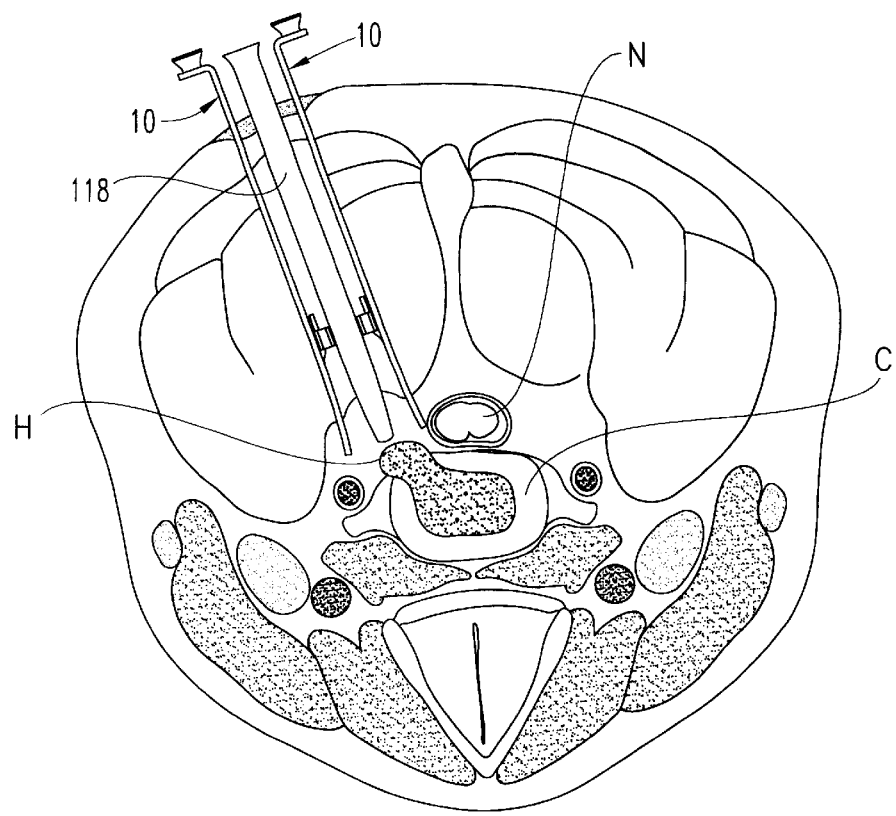
FIG. 26 is an axial view of the tissue retraction system according to the present invention utilized for accessing a herniated disc in the cervical spine.

The present invention contemplates a percutaneous surgical system for use in maintaining a working space at and adjacent to a surgical site. In the illustrated embodiment, the assembly including tissue retractors 10 or 30 and various ring members 50, 65, 70, 72 and 80, are used to implant a fusion cage within the L5-S1 disc space. Of course, the same apparatus can be used at various levels of the spine including the cervical, thoracic and lumbar spine. In addition, the inventive assembly can also be used in various approaches to the spine. As shown in FIG. 21, an anterior approach to the lumbar spine is illustrated. In FIG. 26, a posterior approach to the lumbar spine is shown. Specifically, the assembly is depicted for removing a disc herniation H at a lumbar disc C. In this approach, it can be seen that the tissue retractors 10 create a working space at the site of the disc herniation. In addition, at least one of the tissue retractors 10 are disposed adjacent the spinal cord or neural sheath to protect this sensitive tissue and to prevent access to the spinal cord by the working tools.

Figure 27:
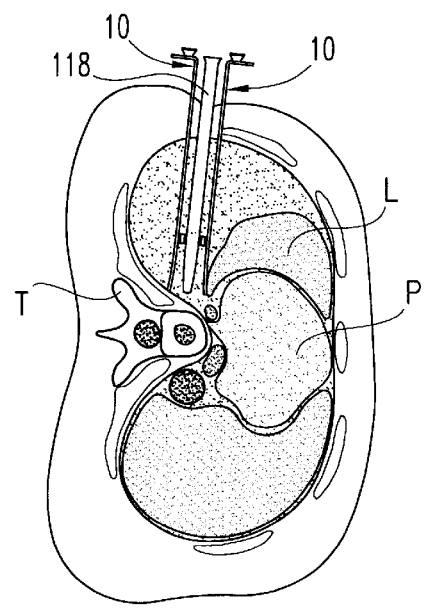
FIG. 27 is an axial view of the tissue retraction system according to the present invention used for a thoracoscopy approach to a thoracic disc space.

An approach to a thoracic vertebra T is shown in FIG. 27. In this instance, a translateral approach is implemented to access a thoracic disc. In this Figure, it is seen that a tissue retractor 10 can be used to retract the lung tissue L as well as tissue associated with the chest cavity P.

Figure 28:
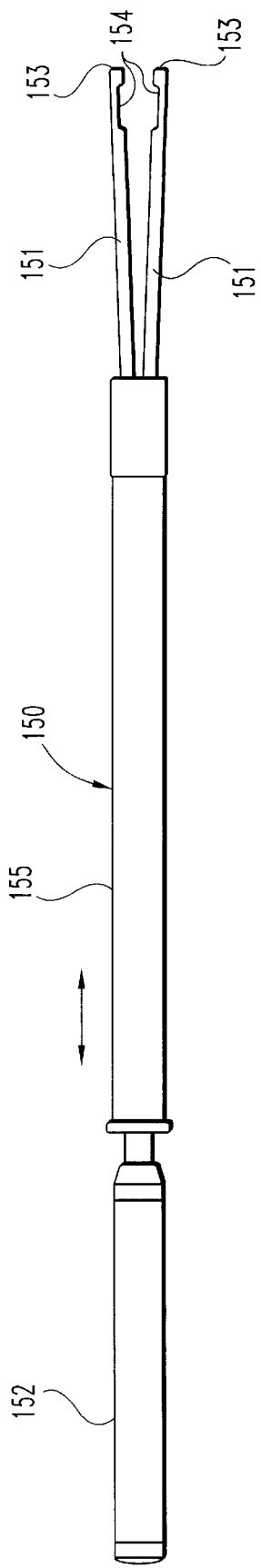
FIG. 28 is a side elevational view of a holder assembly for holding a ring member according to the present invention.

A further component of the present tissue retraction system is a holder assembly 150 shown in FIG. 28 that is configured to hold a ring member, such as a the ring members 50, 65, 70, 72 or 80 described above. In one embodiment, the holder assembly includes a pair of arms 151 mounted to a handle 152. The arms 151 are configured with gripping ends 153, each end 153 defining a recess 154 sized to fit around a wall, such as outer wall 51, or inner wall 54, of a ring member, such as member 50. The arms 151 can be resiliently pressed together so that the gripping ends 153 engage a ring member with a wall trapped within the recesses 154. In a preferred embodiment, a sleeve 155 is slidably disposed about both arms 151. The arms 151 are biased apart, but as the sleeve 155 is advanced towards the gripping ends 153, the arms are resiliently forced together.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A tissue retractor comprising:
    an elongated blade having a proximal end, a distal end, and a length therebetween, said distal end configured for atraumatic contact with body tissue, said blade defining a channel along said length, said channel configured to receive an elongated pin therethrough; and
    a prong attached to said blade between said proximal and distal ends, said prong defining a slot between said blade and said prong, said slot opening toward said proximal end of said blade.

2. The tissue retractor according to claim 1, wherein said elongated blade includes a first portion extending from said proximal end and a second portion extending from said distal end, said second portion being angled relative to said first portion.

3. The tissue retractor according to claim 2, wherein said elongated blade includes a first side and opposite second side, and said second portion being angled away from said first side.

4. The tissue retractor according to claim 3, wherein said prong is attached to said first side.

5. The tissue retractor of claim 3, wherein said channel is defined by a tube attached to said second side and extending along substantially the entire length of said first portion and intersecting said second side of said second portion.

6. The tissue retractor of claim 1, wherein said channel extends between said proximal end and said distal end of said blade.

7. The tissue retractor of claim 6, further comprising a fixation pin having a length greater than the length of said elongated blade and sized to be received within said channel.

8. The tissue retractor assembly according to claim 7, wherein said fixation pin has a tip configured for penetrating bone to anchor said fixation pin.

9. A tissue retractor comprising:
    an elongated blade having a proximal end, a distal end, and a length therebetween, said distal end configured for atraumatic contact with body tissue, said blade having a channel for receiving a fixation pin therethrough;
    a plate portion attached to said blade and projecting outwardly from said proximal end;
    a boss projecting from said plate portion and defining a groove around at least a portion of said boss, wherein said boss includes:
        a base attached to said plate portion; and
        a disc attached to said base, wherein said groove is defined at an intersection of said base and said disc, said disc including a plurality of notches for engaging a manipulation tool.

10. The tissue retractor according to claim 9, wherein said elongated blade includes a first portion extending from said proximal end and a second portion extending from said distal end, said second portion being angled relative to said first portion, and further wherein said channel extends substantially the entire length of said first portion and intersects said second portion to define an opening through said second portion.

11. The tissue retractor according to claim 10, wherein said elongated blade includes a first side and opposite second side, said second portion being angled away from said first side, and further wherein said channel is defined by a tube attached to said second side and extending along substantially the entire length of said first portion and intersecting said second side of said second portion.

12. The tissue retractor according to claim 9, further comprising a prong attached to said blade between said proximal and distal ends, said prong defining a slot between said blade and said prong, said slot opening toward said proximal end of said blade.

13. The tissue retractor of claim 9, wherein said channel extends between said proximal end and said distal end of said blade.

14. The tissue retractor of claim 13, further comprising a fixation pin having a length greater than the length of said elongated blade and sized to be received within said channel.

15. The tissue retractor assembly according to claim 14, wherein said fixation pin has a tip configured for penetrating bone to anchor said fixation pin.

* * * * *